United States Patent
Kim et al.

(10) Patent No.: US 11,439,486 B2
(45) Date of Patent: Sep. 13, 2022

(54) ROOT CANAL TREATMENT APPARATUS

(71) Applicant: SEOUL NATIONAL UNIVERSITY R&DB FOUNDATION, Seoul (KR)

(72) Inventors: Ho-Young Kim, Seoul (KR); Shin Hye Chung, Seoul (KR); Dohyun Jung, Gwangmyeong-Si Gyeonggi-do (KR); Won Jun Shon, Seoul (KR); Junhee Choi, Seongnam-Si Gyeonggi-do (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 237 days.

(21) Appl. No.: 16/690,492

(22) Filed: Nov. 21, 2019

(65) Prior Publication Data
US 2020/0085534 A1    Mar. 19, 2020

Related U.S. Application Data

(63) Continuation of application No. PCT/KR2018/005832, filed on May 23, 2018.

(30) Foreign Application Priority Data

May 24, 2017 (KR) .................. 10-2017-0064117

(51) Int. Cl.
*A61C 17/02* (2006.01)
*A61C 5/50* (2017.01)
*A61C 17/20* (2006.01)

(52) U.S. Cl.
CPC .............. *A61C 17/02* (2013.01); *A61C 5/50* (2017.02); *A61C 17/0208* (2013.01); *A61C 17/20* (2013.01)

(58) Field of Classification Search
CPC ..... A61C 17/02; A61C 17/0208; A61C 17/20; A61C 5/50; A61C 5/40; A61K 6/52
(Continued)

(56) References Cited

U.S. PATENT DOCUMENTS 4,021,921 A * 5/1977 Detaille ............. A61C 17/0208
433/81
5,295,828 A * 3/1994 Grosrey ............. A61C 17/0208
433/224
(Continued)

FOREIGN PATENT DOCUMENTS

JP    H05200054 A    8/1993
KR    20070034577 A    3/2007
(Continued)

OTHER PUBLICATIONS

International Search Report for PCT/KR2018/005832 dated Aug. 30, 2018.

*Primary Examiner* — Jacqueline T Johanas
*Assistant Examiner* — Shannel Nicole Belk
(74) *Attorney, Agent, or Firm* — Dinsmore & Shohl LLP; Yongsok Choi, Esq.

(57) ABSTRACT

The present invention relates to a root canal treatment apparatus for cleaning a root canal, a root canal treatment apparatus for charging a root canal, or a root canal treatment apparatus for cleaning and charging a root canal. The root canal treatment apparatus for cleaning a root canal according to the present invention comprises: a storage container for storing a cleaning liquid or a filler supplied from the outside; an ultrasonic oscillator for applying ultrasonic waves to the cleaning liquid or the filler stored in the storage container; an injection port for injecting, around the root canal, the cleaning liquid or the filler to which the ultrasonic waves have been applied in the storage container; and a nozzle having a suction port for sucking the cleaning liquid or bubbles in the root canal or the bubble.

5 Claims, 13 Drawing Sheets

(58) Field of Classification Search
USPC .......................................................... 433/81
See application file for complete search history.

(56) References Cited

U.S. PATENT DOCUMENTS

| | | | |
|---|---|---|---|
| 8,506,293 B2 | 8/2013 | Pond | |
| 2003/0031978 A1* | 2/2003 | Garman | A61C 5/50 |
| | | | 433/89 |
| 2006/0110710 A1* | 5/2006 | Schemmer | A61K 33/00 |
| | | | 433/81 |
| 2007/0244425 A1* | 10/2007 | Pond | A61C 17/0208 |
| | | | 604/27 |
| 2007/0287125 A1* | 12/2007 | Weill | B08B 9/0321 |
| | | | 433/81 |
| 2011/0076638 A1* | 3/2011 | Gottenbos | A61C 17/02 |
| | | | 15/22.1 |
| 2011/0143305 A1* | 6/2011 | Wagner | A61C 19/063 |
| | | | 433/29 |
| 2013/0040267 A1* | 2/2013 | Bergheim | A61C 17/20 |
| | | | 433/226 |
| 2014/0147804 A1* | 5/2014 | Yamamoto | A61C 17/0208 |
| | | | 433/29 |
| 2015/0030991 A1* | 1/2015 | Sung | A61C 5/40 |
| | | | 261/76 |
| 2015/0064647 A1* | 3/2015 | Wong | A61C 1/07 |
| | | | 433/119 |
| 2015/0111169 A1* | 4/2015 | Yamamoto | A61C 17/0202 |
| | | | 433/86 |
| 2017/0281312 A1* | 10/2017 | Khakpour | A61C 17/024 |
| 2020/0085534 A1* | 3/2020 | Kim | A61C 17/02 |

FOREIGN PATENT DOCUMENTS

| | | |
|---|---|---|
| KR | 20140028079 A | 3/2014 |
| KR | 20150020523 A | 2/2015 |

* cited by examiner

ROOT CANAL TREATMENT APPARATUS

CROSS-REFERENCE TO RELATED APPLICATION

This application is a continuation of International Application No. PCT/KR2018/005832 filed on May 23, 2018, which claims priority to Korean Patent Application No. 10-2017-0064117 filed on May 24, 2017, the entire contents of which are herein incorporated by reference.

TECHNICAL FIELD

The present invention relates to an apparatus for root canal treatment, and more particularly, to an apparatus for root canal treatment, which is capable of cleaning a root canal of a tooth, filling a filling material in the cleaned root canal, and simultaneously performing cleaning and filling of the root canal.

BACKGROUND ART

After Kakeyash et al. demonstrated first in a sterile mouse that bacteria were the primary cause of pulp inflammation in 1967, a biofilm and a necrotic tissue, which are bacteria forming a colony in a root canal, were revealed as major causes of inflammatory response. Therefore, in determining successful endodontic treatment, it is most important to completely remove bacteria and necrotic tissues which are present in the root canal and prevent proliferation.

The treatment of the root canal is performed in three stages including forming a root canal, cleaning the root canal, and filling the root canal.

The cleaning of the root canal is performed after a rotten nerve is primarily removed using an endodontic file, and since the cleaning of the root canal is necessary to remove infected microorganisms, the cleaning of the root canal is an important procedure in a success rate of endodontic treatment.

However, even though contaminants in the root canal have been removed by cleaning to a score zero level (in a case in which a residual amount which is present in a designated portion within the root canal is less than 10%), when a sealing of the root canal seal is incomplete, there is a risk that the remaining bacteria will receive nutrients to multiply. Therefore, a process of sealing the root canal with a filling material after the cleaning is performed.

A passive ultrasonic irrigation (PUI), which is a device for cleaning the root canal by filling a cleaning liquid in a root canal of a tooth and inserting a tip for generating ultrasonic waves in the root canal, is conventionally known. However, there is a problem in that the PUI requires extension of the root canal so as to insert the tip into the root canal, and, when the root canal is severely curved, it is difficult to insert the tip into the root canal.

Further, a method of injecting a filling material into a root canal using a syringe-needle for filling of the root canal is conventionally known. However, there is a limitation in injecting the filling material into a distal end of a tooth due to high viscosity of the filling material and air which is present in the root canal to act as resistance.

SUMMARY

The present invention is directed to providing a root canal treatment device for cleaning a root canal with high cleaning efficiency using both an effect of an injection stream of a cleaning liquid and an effect of bubbles by applying ultrasonic waves to the cleaning liquid accommodated in a storage container to generate and inject bubbles.

The present invention is also directed to providing a root canal treatment device which is capable of effectively filling a filling material in a root canal having a complicated shape by applying ultrasonic waves to the filling material accommodated in a storage container to discharge the filling material to the root canal and, simultaneously, suctioning air in the root canal.

The problems to be solved by the present invention are not limited to those described above, and other problems not mentioned above should be clearly understood by those skilled in the art from the following description.

A root canal treatment apparatus according to an embodiment will be described. One aspect of the present invention provides a root canal treatment apparatus including a storage container configured to store a cleaning liquid supplied from the outside, an ultrasonic oscillator configured to apply ultrasonic waves to the cleaning liquid stored in the storage container, and a nozzle including an injection line in which an injection port for injecting a cleaning liquid, to which ultrasonic waves are applied in the storage container, around a root canal is formed and a suction line in which a suction port for suctioning the cleaning liquid in the root canal is formed, wherein the root canal treatment device cleans the root canal.

According to one aspect, the ultrasonic oscillator may generate bubbles by applying the ultrasonic waves to the cleaning liquid.

According to one aspect, the injection port of the nozzle may be formed as a hole passing straight through, and the suction port of the nozzle may be formed in an annular shape to surround the injection port.

According to one aspect, the nozzle may further include an inclined line in which an inclined port for injecting the cleaning liquid, which is injected from the injection port, at an inclined angle from 0° to 90° is formed and which is formed to protrude from one end of the injection line.

According to one aspect, the inclined port may be provided as one or more inclined ports which are radially formed from a center of one end of the injection port.

According to one aspect, the inclined port may be formed at a center of one end of the injection port to radially inject the cleaning liquid.

According to one aspect, the inclined port may be provided as a plurality of holes formed at an end of the inclined line. According to one aspect, the root canal treatment apparatus may further include a suction pump connected to the suction port of the nozzle. A root canal treatment apparatus according to another embodiment will be described.

Another aspect of the present invention provides a root canal treatment apparatus including a storage container configured to store a filling material for filling of a root canal, an ultrasonic oscillator configured to apply ultrasonic waves to the filling material stored in the storage container, and a nozzle including an injection line in which an injection port for discharging the filling material, to which the ultrasonic waves are applied in the storage container, around a root canal is formed and a suction line in which a suction port for suctioning air in the root canal is formed, wherein the root canal treatment device fills the root canal.

According to one aspect, the root canal treatment device may further include a pressurizing part configured to pressurize the filling material in the storage container to discharge the filling material from the injection port of the nozzle.

According to one aspect, the filling material may be formed of flowable root canal filling materials.

According to one aspect, the injection port of the nozzle may be formed as a hole passing straight through, and the suction port of the nozzle may be formed in an annular shape to surround the injection port.

According to one aspect, the nozzle may further include an inclined line in which an inclined port for injecting the cleaning liquid, which is injected from the injection port, at an inclined angle from 00 to 900 is formed and which is formed to protrude from one end of the injection line.

According to one aspect, the inclined port may be provided as one or more inclined ports which are radially formed from a center of one end of the injection port.

According to one aspect, the inclined port may be formed at a center of one end of the injection port to radially inject the filling material.

According to one aspect, the inclined port may be provided as a plurality of holes formed at an end of the inclined line.

According to one aspect, the root canal treatment apparatus may further include a suction pump connected to the suction port of the nozzle.

A root canal treatment apparatus according to still another embodiment will be described. Still another aspect of the present invention provides a root canal treatment apparatus including a storage container configured to store a cleaning liquid or a filling material for filling of a root canal, an ultrasonic oscillator configured to apply ultrasonic waves to the cleaning liquid or the filling material stored in the storage container, and a nozzle including an injection line in which an injection port for discharging the cleaning liquid or the filling material, to which the ultrasonic waves are applied in the storage container, around a root canal is formed and a suction line in which a suction port for suctioning the cleaning liquid or air in the root canal is formed, wherein the root canal treatment device cleans and fills the root canal.

According to one aspect, the root canal treatment apparatus may further include a cleaning liquid storage connected to the storage container and configured to supply the cleaning liquid to the storage container, and a filling material storage connected to the storage container and configured to supply the filling material to the storage container.

According to one aspect, the filling material may be formed of flowable root canal filling materials.

According to one aspect, the injection port of the nozzle may be formed as a hole passing straight through, and the suction port of the nozzle may be formed in an annular shape to surround the injection port.

According to one aspect, the nozzle may further include an inclined line in which an inclined port for injecting the cleaning liquid or the filling material, which is injected from the injection port, at an inclined angle from 0° to 90° is formed and which is formed to protrude from one end of the injection line.

According to one aspect, the inclined port may be provided as one or more inclined ports which are radially formed from a center of one end of the injection port.

According to one aspect, the inclined port may be formed at a center of one end of the injection port to radially inject the cleaning liquid or the filling material.

According to one aspect, the inclined port may be provided as a plurality of holes formed at an end of the inclined line.

According to one aspect, the root canal treatment apparatus may further include a suction pump connected to the suction port of the nozzle.

As described above, in accordance with a root canal treatment device of the present invention, bubbles are generated in a cleaning liquid in a storage container using ultrasonic waves and the cleaning liquid is injected such that there is an advantage in which high cleaning efficiency can be achieved using a cleaning effect of a root canal due to an injection stream as well as a cleaning effect due to the bubbles.

Further, injection of the cleaning liquid through the injection port and suction of the cleaning liquid of the root canal through the suction port disposed adjacent to the injection port are simultaneously performed such that there is an advantage in that the cleaning efficiency can be improved and, at the same time, side effects due to leakage of the cleaning liquid can be prevented.

Further, the ultrasonic waves are applied to the filling material having high viscosity to disperse fine particles bonded to each other in the filling material, thereby lowering the high viscosity, and air in the root canal is suctioned to remove resistance due to the air such that there is an advantage in that the filling material can densely fill up to a distal end of a tooth.

The effects of the root canal treatment apparatuses according to the embodiments are not limited to the above-mentioned effects, and other effects not mentioned above can be clearly understood by those skilled in the art from the foregoing description.

DETAILED DESCRIPTION

Figure 1A:
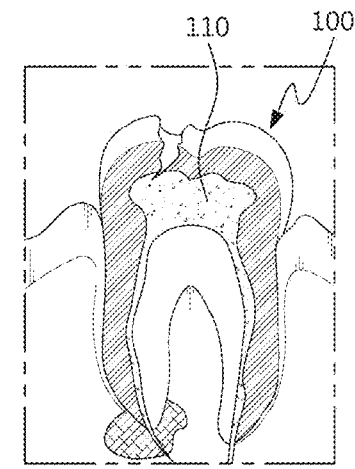
FIG. 1A is a schematic diagram illustrating a state in which inflammation occurs in pulp tissue during a root canal treatment process.

This patent application claims a priority based on Korean Patent Application No. 2017-0064117, filed on May 24, 2017, the entire contents of which are hereby incorporated by reference.

Hereinafter, exemplary embodiments will be described in detail with reference to the accompanying drawings. In giving reference numerals to components of the drawings, the same reference numerals are given to the same components even though the same components are shown in different drawings. Further, in the following description of the embodiments, when a detailed description of related known configurations or functions is determined to obscure the gist of the present invention, the detailed description thereof will be omitted.

Furthermore, in describing components of the embodiments, a first, a second. A, B, (a), (b), and the like can be used. These terms are intended to distinguish one component from other components, but the nature and the order or sequence of the components is not limited by those terms. When components are disclosed as "connected." "coupled" or "contacted" to other components, the component can be directly connected or contacted to the other components, but it should be understood that another component(s) could be "connected," "coupled" or "contacted" therebetween.

A component included in any one embodiment and a component including a common function will be described using the same name in other embodiments. Unless stated to the contrary, a description in any one embodiment may be applied to other embodiments, and detailed descriptions thereof will be omitted in the overlapping range.

Hereinafter, the present invention will be described with reference to the accompanying drawings for describing root canal treatment apparatuses according to the embodiments of the present invention.

First, prior to describing a root canal treatment apparatus according to the present invention, a process of treating a root canal will be described.

FIGS. 1A to 1D are diagrams illustrating a root canal treatment process.

Figure 1B:
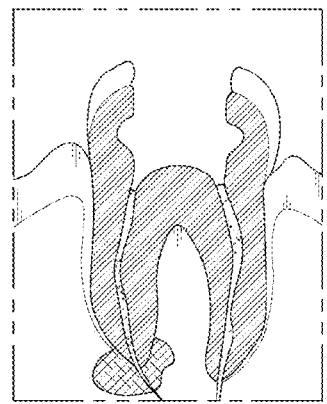
FIG. 1B is a schematic diagram illustrating a state in which infected pulp tissue is removed during the root canal treatment process.
Figure 1C:
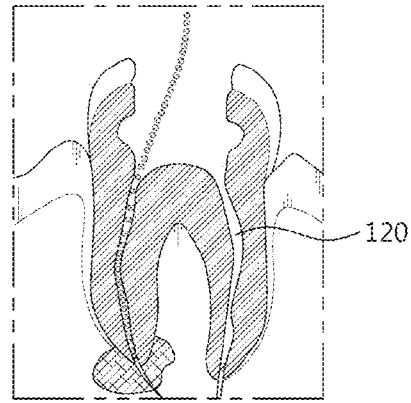
FIG. 1C is a schematic diagram illustrating a state in which the pulp tissue of a root canal is removed during the root canal treatment process.
Figure 1D:
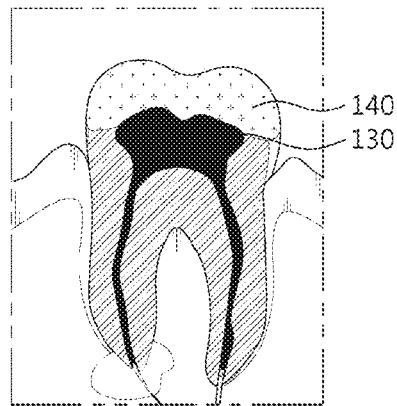
FIG. 1D is a schematic diagram illustrating a state in which a filling material fills during the root canal treatment process.

FIG. 1A is a schematic diagram illustrating a state in which inflammation occurs in pulp tissue during a root canal treatment process, FIG. 1B is a schematic diagram illustrating a state in which infected pulp tissue is removed during the root canal treatment process, FIG. 1C is a schematic diagram illustrating a state in which the pulp tissue of a root canal is removed during the root canal treatment process, and FIG. 1D is a schematic diagram illustrating a state in which a filling material fills during the root canal treatment process.

Unlike an appearance of a tooth 100, the tooth 100 has a soft tissue which has rich nerves and rich blood vessels and is called a dental pulp 110. The dental pulp 110 extends to the root of a tooth. i.e., a dental root, and is connected to a blood vessel and a nerve of a periodontal ligament in ulitis surrounding the dental root through a hole (root apex hole) at an end of the root of a tooth.

As shown in FIG. 1A, when a tissue of the dental pulp 110 is infected and thus inflammation occurs, as shown in FIG. 1B, an opening is formed to access to an interior of the tooth 100 and the infected tissue of the dental pulp 110 is removed.

In this case, as shown in FIG. 1C, the dental pulp 110 in the root of a tooth (the dental root) as well as a pulp cavity are removed using a tissue removal device (endodontic file) designed to enter the root canal 120, and the root canal 120 is cleaned with a cleaning liquid to remove any remaining tissue of the dental pulp 110 or denatured dental tissues.

Next, as shown FIG. 1D, a separate filling material 130 fills in the root canal 120 and an inlet is sealed with a crown 140 to prevent bacterial growth in the root canal 120.

The apparatus for root canal treatment of the present invention, which will be described below, relates to root canal treatment apparatuses 200 and 300 for performing cleaning of the root canal 120, a root canal treatment apparatus 400 for filling the filling material 130 in the root canal 120, and a root canal treatment apparatus 500 for performing cleaning and filling of a root canal.

First, the root canal treatment apparatus 200 for performing cleaning in the root canal 120 according to one embodiment of the present invention will be described with reference to FIGS. 2 to 4.

Figure 2:
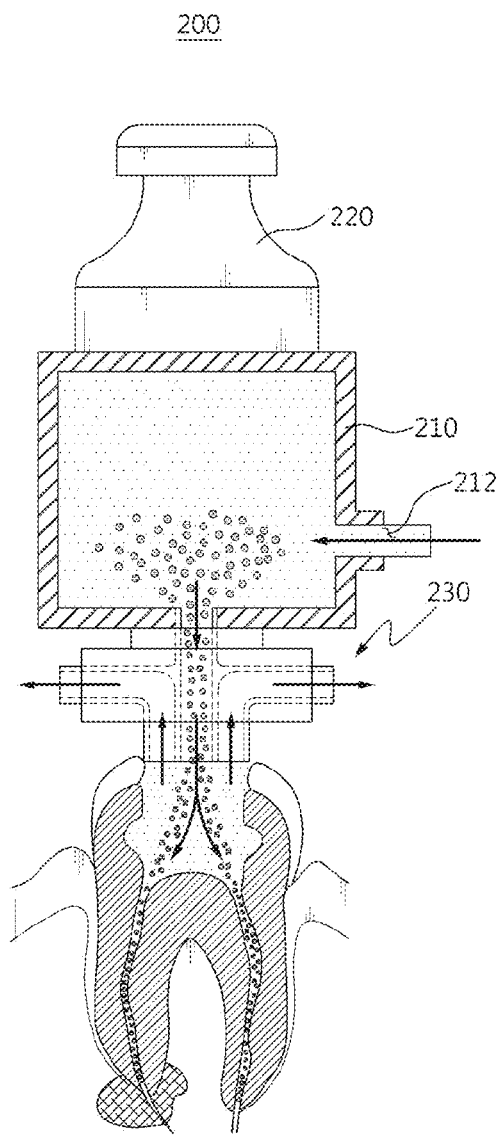
FIG. 2 is a diagram illustrating a root canal treatment apparatus according to one embodiment of the present invention.

FIG. 2 is a diagram illustrating a root canal treatment apparatus according to one embodiment of the present invention. FIG. 3 is a side cross-sectional view illustrating a nozzle according to one embodiment of the present invention, FIG. 4 is a bottom view of FIG. 3, and FIG. 5 shows enlarged photographs illustrating a process of performing cleaning using the root canal treatment apparatus according to the present invention.

The root canal treatment apparatus 200 according to one embodiment of the present invention may include a storage container 210, an ultrasonic oscillator 220, and a nozzle 230.

The storage container 210 receives a cleaning liquid stored in a cleaning liquid storage (not shown), which is separately provided to the outside, by a pump or the like and accommodates the cleaning liquid in the storage container 210. An inlet 212 to which the cleaning liquid is supplied may be formed at one side of the storage container 210.

In this case, 1 to 5 sodium hypochlorite (NaOCl) may be used as the cleaning liquid stored in the cleaning liquid storage, but the present invention is not limited thereto.

The ultrasonic oscillator 220 is formed inside or outside the storage container 210 to apply ultrasonic waves to the cleaning liquid accommodated in the storage container 210. In this case, it is preferable to adjust a frequency of the ultrasonic oscillator 220 such that bubbles B are formed in the cleaning liquid due to the ultrasonic waves. When the ultrasonic waves are applied to the cleaning liquid, nuclei which are present in the cleaning liquid in a rarefaction portion with a low negative pressure may form cavitation bubbles B. Further, a flow rate is increased when the cleaning liquid passes through an injection port 232 of the nozzle 230, which will be described below. In this case, the bubbles B in the storage container 210 may be changed to micro bubbles having smaller sizes.

The bubbles B vibrate at the same frequency as the frequency of the ultrasonic waves, and contaminants around the bubbles B may be removed due to such a vibration. Further, when the bubbles B collapse in a portion in which the negative pressure is high, a micro jet is injected to obtain a cleaning effect due to the micro jet.

The nozzle 230 injects the cleaning liquid, to which the ultrasonic waves are applied in the storage container 210, around the root canal 120. In this case, an injection line 231 having the injection port 232 for injecting a cleaning liquid to which ultrasonic waves are applied around the root canal 120 and a suction line 233 having a suction port 234 for sucking the cleaning liquid of the root canal 120 may be formed in the nozzle 230.

Figure 3:
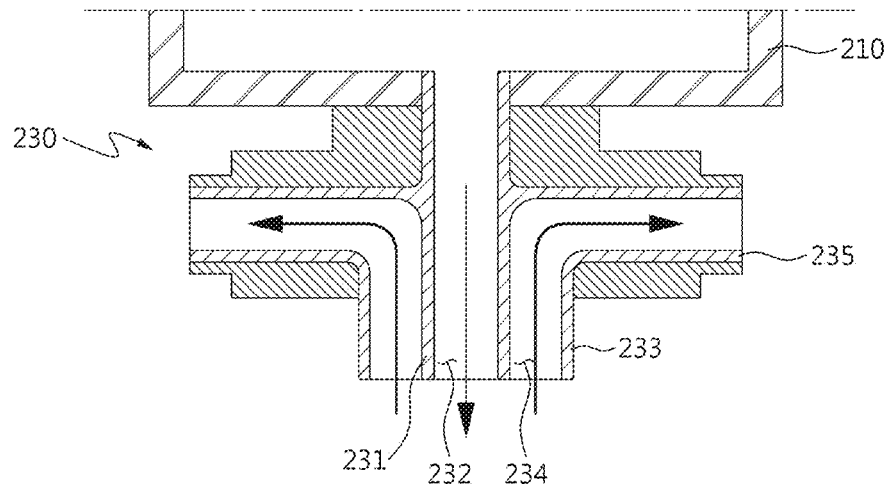
FIG. 3 is a side cross-sectional view illustrating a nozzle according to one embodiment of the present invention.
Figure 4:
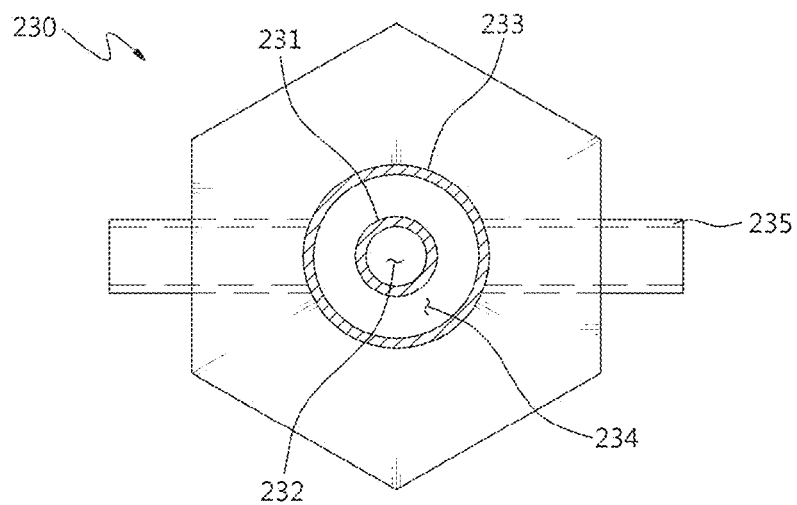
FIG. 4 is a bottom view of FIG. 3.
Figure 5:
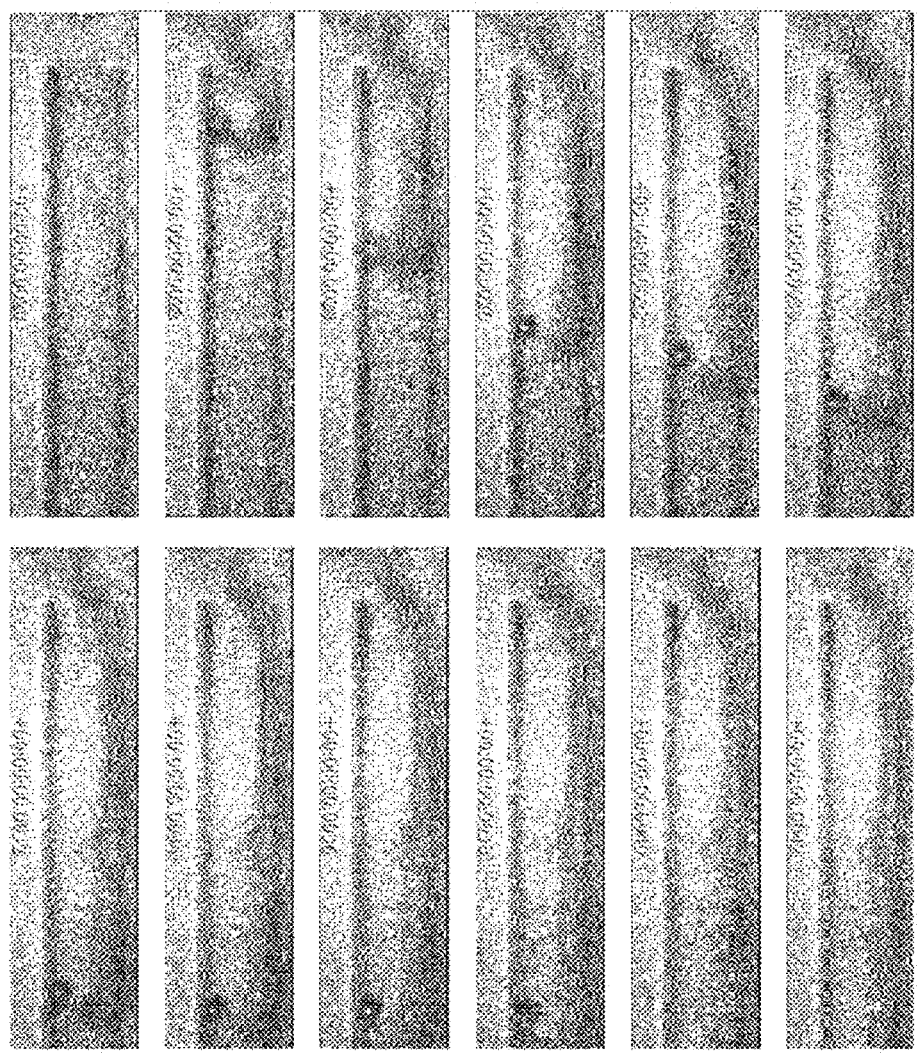
FIG. 5 shows enlarged photographs illustrating a process of performing cleaning using the root canal treatment apparatus according to the present invention.

Preferably, as shown in FIGS. 3 and 4, the injection port 232 is formed as a hole passing straight through the injection line 231 to inject the cleaning liquid, in which the ultrasonic waves in the storage container 210 is applied to generate the bubbles B, around the root canal 120, and the suction port 234 is formed in an annular shape to surround the injection port 232 and suctions the cleaning liquid located in the root canal 120 again after cleaning to discharge the suctioned cleaning liquid to the outside through a discharge line 235. Therefore, in order to suction the cleaning liquid through the suction port 234, a suction pump (not shown) may be connected to the suction port 234.

The cleaning liquid discharged through the injection port toward the root canal 120 may cause side effects of pain or necrosis of a tissue when passing through a portion of a root apex to be discharged to a gum. Thus, the cleaning liquid is suctioned through the suction port 234 such that it is possible to prevent the cleaning liquid from leaking out of the tooth during the procedure. Further, since an injection direction of the nozzle faces a straight direction or an inner wall portion of the tooth, even in various types of root canals, the cleaning liquid may be simultaneously uniformly introduced, thereby not leaking out of the tooth.

Further, the cleaning with the cleaning liquid discharged through the injection port 232 and discharging the cleaning liquid through the suction port 234 after the cleaning are simultaneously continuously performed. Consequently, the contaminated cleaning liquid after the cleaning is removed and a new cleaning liquid is supplied such that a smooth circulation of the cleaning liquid is induced and thus cleaning efficiency may be further improved.

Hereinafter, an operation of performing cleaning using the root canal treatment apparatus 200, which is described with reference to FIGS. 2 to 4, will be described.

The cleaning liquid may be continuously supplied into the storage container 210 by a pump from the cleaning liquid storage in which the cleaning liquid is stored.

In this case, the ultrasonic oscillator 220 applies ultrasonic waves to the cleaning liquid stored in the storage container 210 to generate a vibration. In this case, it is preferable to apply the ultrasonic waves to form the bubbles B in the cleaning liquid.

The cleaning liquid, in which the bubbles B are generated by applying the ultrasonic waves, is injected around the root canal 120 through the injection port 232 of the nozzle 230. In the present invention, since a solid material such as a cannula is not inserted, conservative cleaning is possible without requiring separate extension of the root canal 120.

Further, since the cleaning is performed by an injection stream discharged from the nozzle 230, the cleaning liquid easily penetrates into the root canal 120 of a narrow tooth such that excellent cleaning power may be obtained at a distal end portion of the tooth.

Further, the injection stream of the cleaning liquid to which the ultrasonic waves are applied has several advantages as compared to an injection stream to which the ultrasonic waves are not applied. First, when the injection stream to which the ultrasonic waves are applied flows along an inner wall of the root canal 120, a thickness of a boundary layer generated on a major surface of the inner wall of the root canal 120 becomes smaller due to an ultrasonic vibration. Owing to an effect in which the thickness of the boundary layer becomes smaller, a dynamic pressure of the injection stream, which is a main cleaning principle of the present invention, may be more effectively transferred to contaminants. Second, the cavitation bubbles B which are present in the injection stream vibrates and ruptures in an ultrasonic field and, owing to a cleaning effect resulting from the vibration and the rupture the cavitation bubbles B, a more excellent cleaning effect may be obtained. A mechanism by which the cleaning is performed through the cleaning liquid in which the bubbles B are generated due to the ultrasonic waves is shown in chronological order in FIG. 5 according to the present invention.

In this case, the cleaning liquid may be injected through the injection port 232 and, simultaneously, the cleaning liquid after the cleaning may be suctioned through the suction port 234 formed around the injection port 232. In this case, a suction pressure may be controlled using a suction pump (not shown). It is preferable to control the cleaning liquid with a pressure not exceeding a central venous pressure (CVP) so as to prevent the cleaning liquid from leaking to the gum around a portion of the root apex.

As described above, the injection of the cleaning liquid through the injection port 232 and the suctioning of the cleaning liquid through the suction port 234 are simultaneously performed. A smooth flow of the cleaning liquid may be induced to improve cleaning efficiency and, simultaneously, during the procedure, it is possible to prevent the cleaning liquid from leaking out of the teeth to cause side effects. Further, since an injection direction of the nozzle faces a straight direction or an inner wall portion of the tooth, even in various types of root canals, the cleaning liquid may be simultaneously uniformly introduced, thereby not leaking out of the tooth.

Hereinafter, the root canal treatment apparatus 300 for performing cleaning in the root canal 120 according to another embodiment of the present invention will be described with reference to FIGS. 6 to 7.

Figure 6:
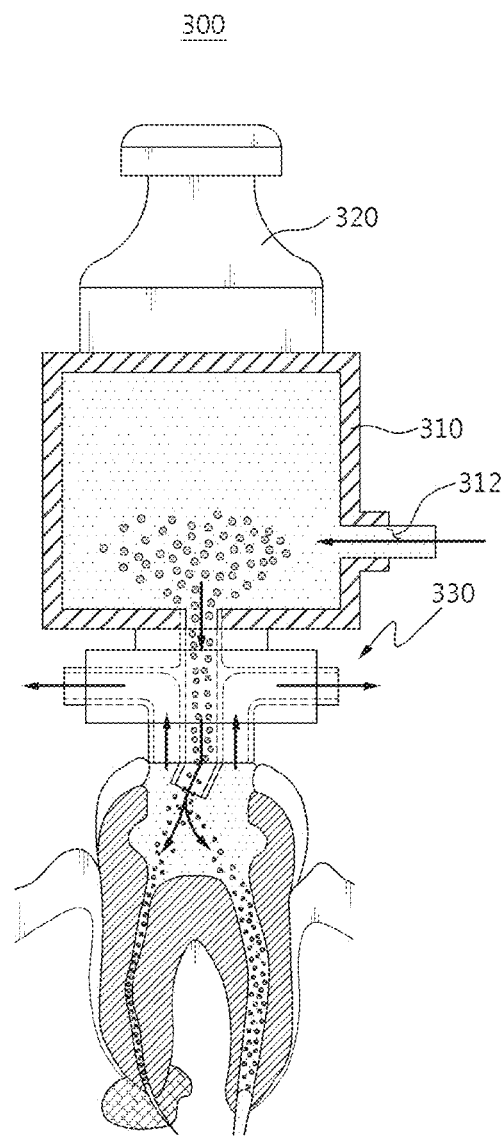
FIG. 6 is a diagram illustrating a root canal treatment apparatus according to another embodiment of the present invention.
Figure 7:
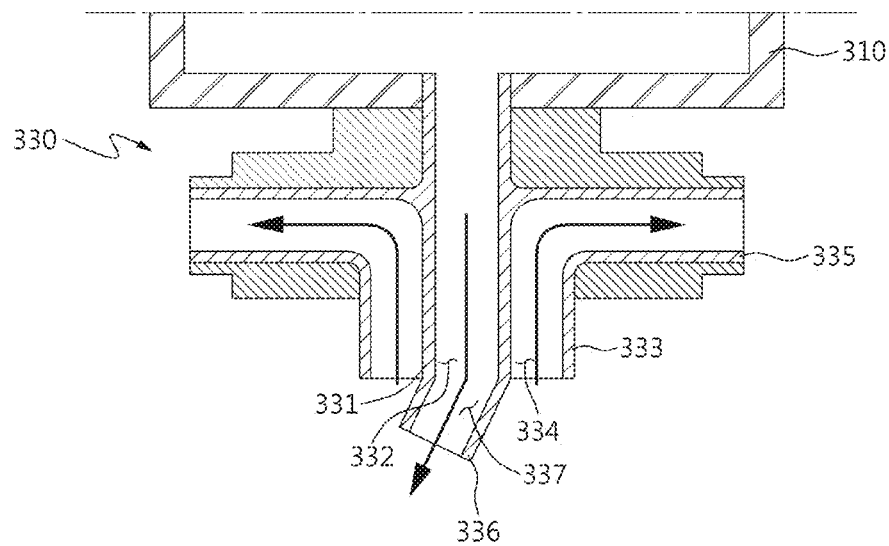
FIG. 7 is a side cross-sectional view illustrating a nozzle according to another embodiment of the present invention.

Referring to FIGS. 6 to 7, the root canal treatment apparatus 300 may include a storage container 310, an ultrasonic oscillator 320, and a nozzle 330.

The storage container 310 and the ultrasonic oscillator 320 includes the same components as compared to the root canal treatment apparatus 200 of one embodiment, and thus descriptions thereof will be omitted.

The nozzle 330 injects the cleaning liquid, to which the ultrasonic waves are applied in the storage container 310, around the root canal 120. In this case, the nozzle 330 may include an injection line 331 in which an injection port 332 for injecting the cleaning liquid to which ultrasonic waves are applied is formed, a suction line 333 in which a suction port 334 for suctioning the cleaning liquid from the root canal 120 is formed, an inclined line 336 which is formed to protrude from one end of the injection line 331 and in which an inclined port 337 for injecting the cleaning liquid injected from the injection port 332 at an inclined angle from 0° to 90° is formed.

The injection port 332 is formed as a hole passing straight through the injection line 331 to inject the cleaning liquid, which the bubbles B are generated by applying the ultrasonic waves in the storage container 310, around a center of the root canal 120. The inclined port 337 injects the cleaning liquid from the center of the root canal 120 at an inclined angle from 0° to 90°.

For example, as shown in FIG. 6, root canals 120 may be formed with different cross-sectional areas. In this case, in order for the cleaning liquid to infiltrate into a root canal having a small cross-sectional area among the root canals 120 having different cross-sectional areas, the cleaning liquid requires a larger pressure than a pressure required to infiltrate into a root canal having a large cross-sectional area thereamong. In this case, when the injection port 332 straight injects the cleaning liquid to the center of the root canal 120, the cleaning liquid is introduced into only the root canal having the large cross-sectional area such that it difficult to clean the root canal having the small cross-sectional area. In order to clean the root canal having the small cross-sectional area, a flow rate of the injected cleaning liquid should be increased. However, in this case, the cleaning liquid may leak into the gum by passing through a root apex of the root canal having the large cross-sectional area.

Here, the root canal treatment apparatus 300 according to another embodiment may inject the cleaning liquid at an inclined angle from 0° to 90° through the inclined port 337. The inclined port 337 may inject the cleaning liquid at the inclined angle to uniformly clean a plurality of root canals 120 having different cross-sectional areas and control an injection direction of the inclined port so as to prevent the cleaning liquid from leaking to the gum. Further, the cleaning liquid may not be leaked to the gum by passing through the root apex of the root canal and may be suctioned through the suction port 334 to be discharged to the outside through a discharge line 335.

Meanwhile, the root canal treatment apparatus 300 may inject the cleaning liquid at the inclined angle from 0° to 90° through the inclined port 337 in a direction of the root canal having the large cross-sectional area. In this case, the cleaning liquid may be introduced into the root canal having the large cross-sectional area but not into the root canal having the small cross-sectional area. The injection of the cleaning liquid through the injection port 332 and the suctioning of the cleaning liquid through the suction port 334 are simultaneously performed. A smooth flow of the cleaning liquid may be induced to improve cleaning efficiency and, simultaneously, during the procedure, it is possible to prevent the cleaning liquid from leaking out of the tooth to cause side effects. Further, since an injection direction of the nozzle faces a straight direction or an inner wall portion of the tooth, even in various types of root canals, the cleaning liquid may be simultaneously uniformly introduced, thereby not leaking out of the tooth.

Hereinafter, the root canal treatment apparatus 400 for performing cleaning in the root canal 120 according to still another embodiment of the present invention will be described with reference to FIG. 8. The root canal treatment apparatus 400 according to still another embodiment of the present invention may include a storage container 310, an ultrasonic oscillator 320, and a nozzle 430. Here, the storage container 310 and the ultrasonic oscillator 320 include the same components as compared to the root canal treatment apparatus 200 of one embodiment, and thus descriptions and drawings thereof will be omitted herein.

Figure 8:
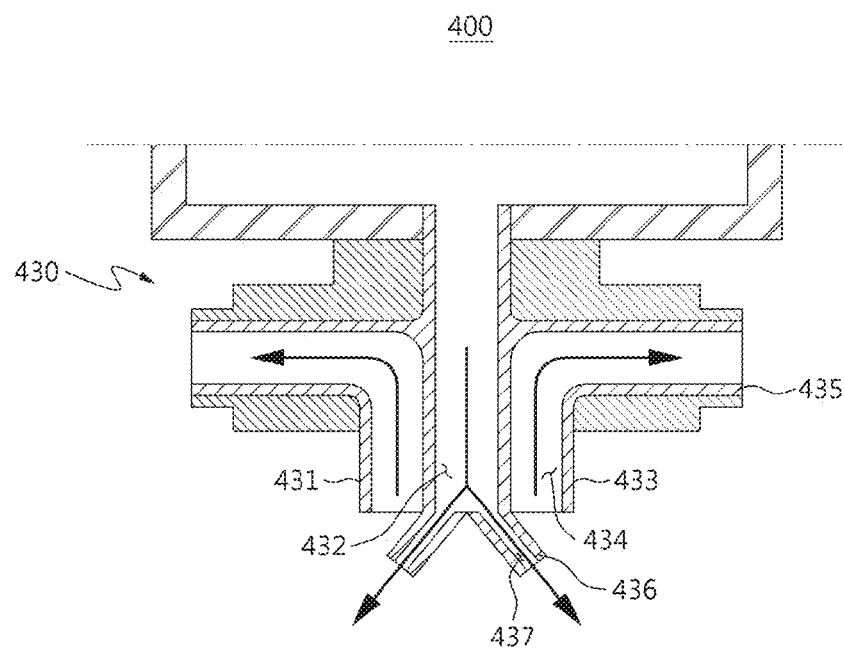
FIG. 8 is a side cross-sectional view illustrating a nozzle according to still another embodiment of the present invention.

FIG. 8 is a side cross-sectional view illustrating a nozzle according to yet another embodiment of the present invention.

Referring to FIG. 8, the nozzle 430 injects the cleaning liquid, to which the ultrasonic waves are applied in the storage container 310, around the root canal 120. In this case, the nozzle 430 may include an injection line 431 in which an injection port 432 for injecting a cleaning liquid to which ultrasonic waves are applied is formed, a suction line 433 in which a suction port 434 for suctioning the cleaning liquid from the root canal 120 is formed, a discharge line 435 connected to the suction port 434 and configured to discharge the suctioned cleaning liquid to the outside, and an inclined line 436 in which an inclined port 437 for injecting the cleaning liquid injected from the injection port 432 at an inclined angle from 0° to 90° is formed and which is formed to protrude from one end of the injection line 331.

The injection port 432 is formed as a hole passing straight through the injection line 431 to inject the cleaning liquid, which the bubbles B are generated by applying the ultrasonic waves in the storage container 310, around the center of the root canal 120.

Here, a plurality of inclined ports 437 are provided to inject the cleaning liquid from the center of the root canal 120 at the inclined angle from 0° to 90°. For example, the inclined line 436 in which the inclined port 437 is formed may be formed to protrude from one end of the injection direction of the cleaning liquid of the injection line 431, and one or more inclined lines 436 may be provided and radially disposed. However, the present invention is not limited thereto, and one inclined line 436 may be formed to protrude from one end of the injection line, and a plurality of inclined ports 437 may be formed in the one inclined line 436. The number of inclined port 437 is not limited and may be appropriately changed according to the number and arrangement of the root canals 120.

The plurality of inclined ports 437 may inject the cleaning liquid at the inclined angle in multiple directions to uniformly clean a plurality of root canals regardless of a cross-sectional area and control the injection direction of the cleaning liquid so as to prevent the cleaning liquid from leaking to the gum. Further, the cleaning liquid may not be leaked to the gum by passing through the root apex of the root canal and may be suctioned through the suction port 434 to be discharged to the outside through a discharge line 335.

The injection of the cleaning liquid through the injection port 437 and the suctioning of the cleaning liquid through the suction port 434 are simultaneously performed. A smooth flow of the cleaning liquid may be induced to improve cleaning efficiency and, simultaneously, during the procedure, it is possible to prevent the cleaning liquid from leaking out of the tooth to cause side effects. Further, since an injection direction of the nozzle 430 faces a straight direction or an inner wall portion of the tooth, even in various types of root canals, the cleaning liquid may be simultaneously uniformly introduced, thereby not leaking out of the tooth.

Hereinafter, the root canal treatment apparatus 500 for performing cleaning in the root canal 120 according to yet another embodiment of the present invention will be described with reference to FIGS. 9 and 10. The root canal treatment apparatus 500 according to yet another embodiment of the present invention may include a storage container 310, an ultrasonic oscillator 320, and a nozzle 530. Here, the storage container 310 and the ultrasonic oscillator 320 include the same components as compared to the root canal treatment apparatus 200 of one embodiment, and thus descriptions and drawings thereof will be omitted herein.

Figure 9:
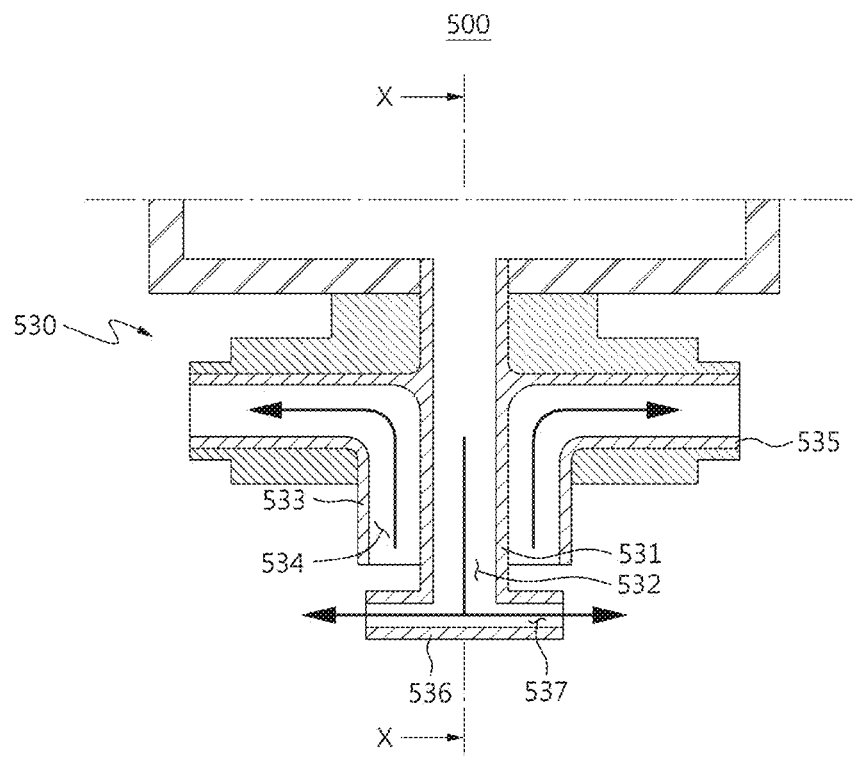
FIG. 9 is a side cross-sectional view illustrating a nozzle according to yet another embodiment of the present invention.
Figure 10:
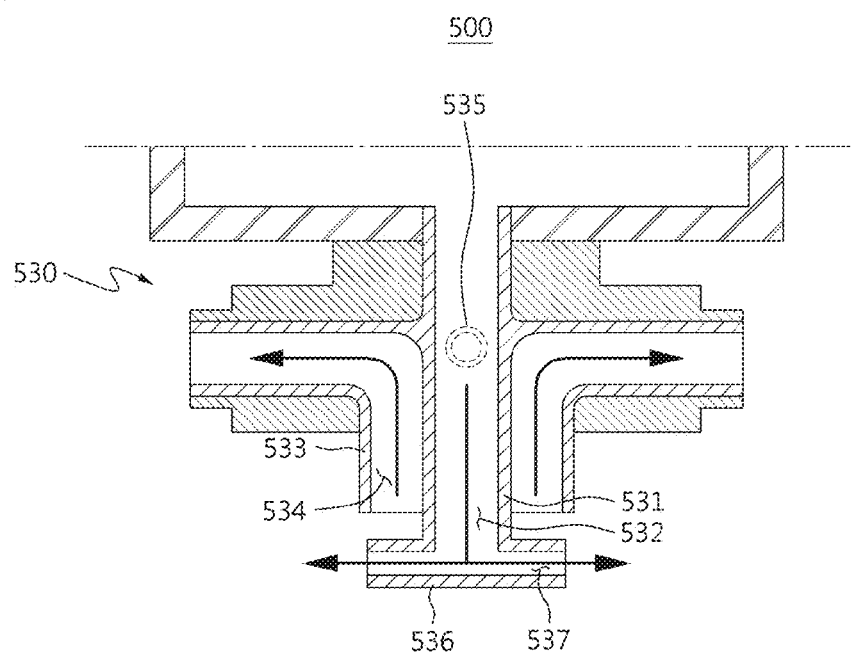
FIG. 10 is a cross-sectional view taken along line X-X of FIG. 9.

FIG. 9 is a side cross-sectional view illustrating a nozzle according to yet another embodiment of the present invention, and FIG. 10 is a cross-sectional view taken along line X-X of FIG. 9.

Referring to FIGS. 9 and 10, the nozzle 530 injects the cleaning liquid, to which the ultrasonic waves are applied in the storage container 310, around the root canal 120. In this case, the nozzle 530 may include an injection line 531 in which an injection port 532 for injecting a cleaning liquid to which ultrasonic waves are applied is formed, a suction line 533 in which a suction port 534 for suctioning the cleaning liquid from the root canal 120 is formed, a discharge line 535 connected to the suction port 534 and configured to discharge the cleaning liquid to the outside, and an inclined line 536 in which an inclined port 537 for radially injecting the cleaning liquid, which is injected from the injection port 532, at a center of one end of the injection port 532 is formed and which is formed to protrude from one end of the injection line 531.

For example, the inclined port 537 may extend from the injection port 532 and may be formed throughout along a circumference of an outer surface of the inclined line 536. In other words, the inclined port 537 may be formed to radially inject the cleaning liquid at the center of one end of the injection port 532. In this case, the inclined port 537 may be formed to inject the cleaning liquid in an injection direction at an inclined angle from 0° to 90°.

The injection port 532 is formed as a hole passing straight through the injection line 531 to inject the cleaning liquid, which the bubbles B are generated by applying the ultrasonic waves in the storage container 310, around a center of the root canal 120. The inclined port 537 radially injects the cleaning liquid, which is injected from the injection port 532, at the inclined angle from 0° to 90° based on concentricity of the injection port 532.

In this case, the inclined port 537 radially injects the cleaning liquid at the inclined angle from the center of the root canal 120. Consequently, the inclined port 537 may uniformly clean a plurality of root canals regardless of cross-sectional areas thereof and prevent the cleaning liquid from leaking to the gum.

Hereinafter, the root canal treatment apparatus 600 for performing cleaning in the root canal 120 according to yet another embodiment of the present invention will be described with reference to FIGS. 11 and 12. The root canal treatment apparatus 600 according to yet another embodiment of the present invention may include a storage container 310, an ultrasonic oscillator 320, and a nozzle 630. Here, the storage container 310 and the ultrasonic oscillator 320 include the same components as compared to the root canal treatment apparatus 200 of one embodiment, and thus descriptions and drawings thereof will be omitted herein.

Figure 11:
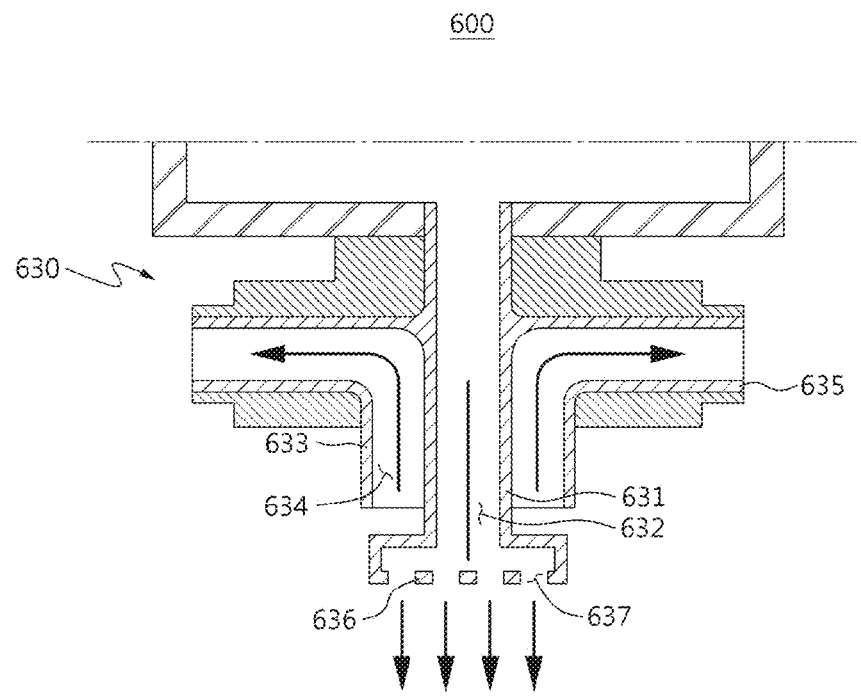
FIG. 11 is a side cross-sectional view illustrating a nozzle according to yet another embodiment of the present invention.
Figure 12:
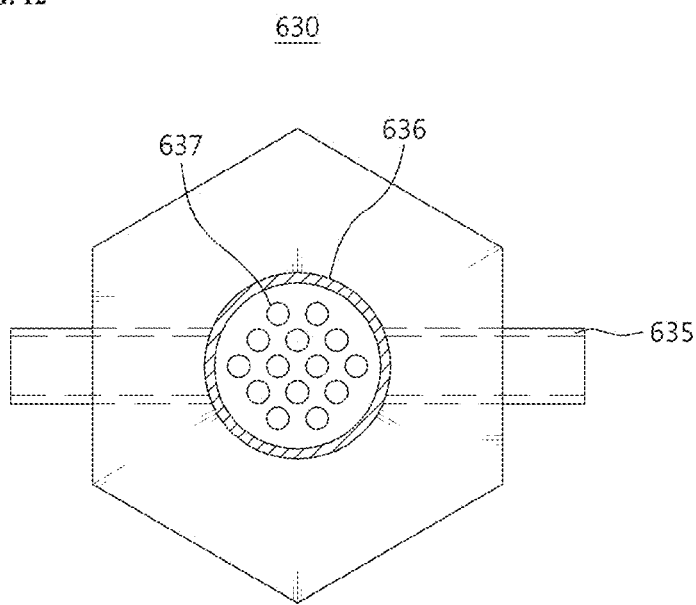
FIG. 12 is a bottom view of FIG. 11.

FIG. 11 is a side cross-sectional view illustrating a nozzle according to yet another embodiment of the present invention, and FIG. 12 is a bottom view of FIG. 11.

Referring to FIGS. 11 and 12, the nozzle 630 injects the cleaning liquid, to which the ultrasonic waves are applied in the storage container 310, around the root canal 120. In this case, the nozzle 630 may include an injection line 631 in which an injection port 632 for injecting a cleaning liquid to which ultrasonic waves are applied is formed, a suction line 633 in which a suction port 534 for suctioning the cleaning liquid from the root canal 120 is formed, a discharge line 635 connected to the suction port 634 and configured to discharge the cleaning liquid to the outside, and an inclined line 636 in which an inclined port 637 for injecting the cleaning liquid, which is injected from the injection port 632, around the root canal 120 and which is formed to protrude from one end of the injection line 631.

A plurality of inclined ports are formed at an end of the inclined line 636 in a direction of the root canal 120. For example, a plurality of inclined ports 637 may be formed to be spaced predetermined intervals on a surface of one end of the inclined line 636, i.e., on a surface thereof toward the root canal 120. Since the inclined port 637 is formed to have a cross-sectional area that is smaller than that of the injection port, a plurality of inclined ports 637 may be provided in the surface of one end of the inclined line.

The plurality of inclined port 637 distributes the cleaning liquid injected from the injection port 632 to inject the distributed cleaning liquid to the root canal 120. In this case, since the cleaning liquid injected to the root canal 120 is injected as a plurality of streams having small cross-sectional areas, the cleaning liquid may uniformly clean regardless of a cross-sectional area of the root canal 120 and may not leak to the gum.

Meanwhile, the plurality of inclined ports 637 may be formed to inject the cleaning liquid in an injection direction at an inclined angle from 0° to 90°. For example, a center of the surface of one end of the inclined line 636 may have a shape protruding than an outer peripheral of the surface thereof, and the inclined port 637 may be formed along the surface of the inclined line 636 to inject the cleaning liquid at a predetermined angle. However, the present invention is not limited thereto, and each of the plurality of inclined ports may be formed to have a predetermined angle.

Meanwhile, even though the contaminants in the root canal 120 are removed to a score zero level with the above-described root canal treatment apparatuses 200 and 300, when a sealing of the root canal 120 is not complete, there is a risk in that the bacteria remaining in the root canal 120 receives nutrients to multiply.

Therefore, a configuration of a root canal treatment apparatus, which will be described below, is similar to that of the above-described root canal treatment apparatus 200 but fills the filling material 130 in the root canal 120. Hereinafter, a root canal treatment apparatus for filling the filling material 130 in the root canal 120 according to yet another embodiment of the present invention will be described with reference to FIGS. 13 and 14A to 14C.

Figure 13:
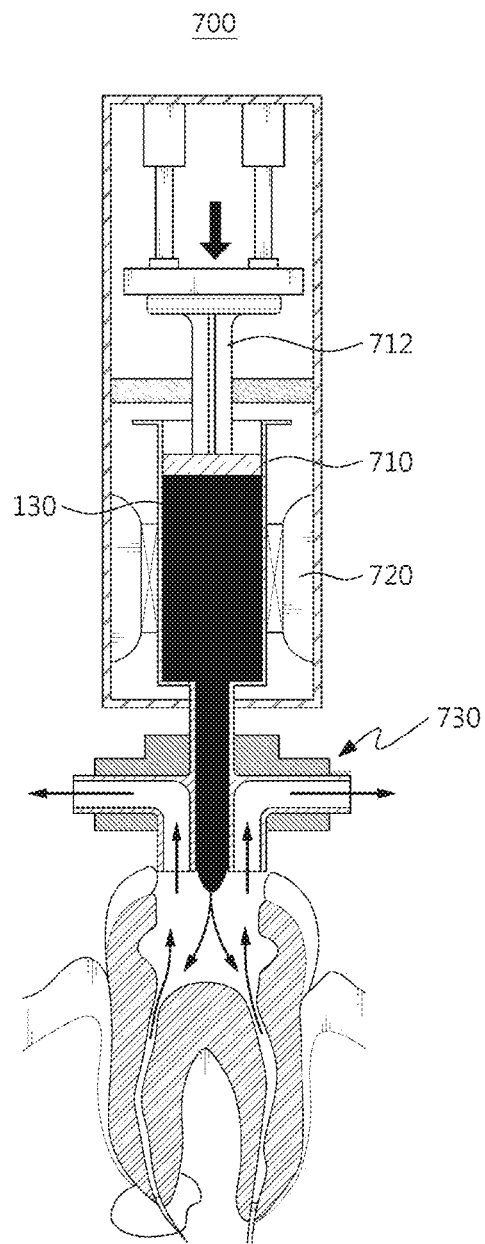
FIG. 13 is a diagram illustrating a root canal treatment apparatus according to yet another embodiment of the present invention.
Figure 14A:
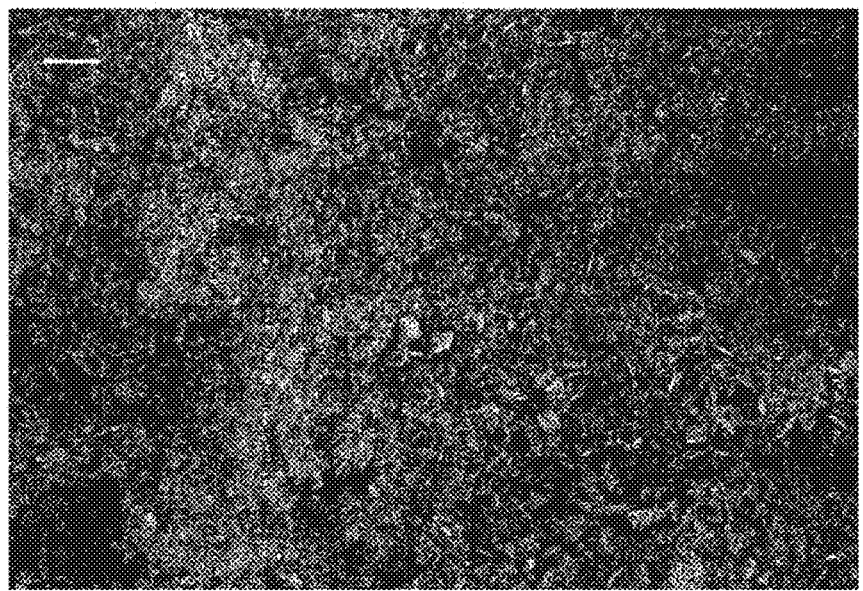
FIG. 14A is an enlarged photograph illustrating a filling result when filling of a root canal is performed with pressurization of only a pressurizing part of FIG. 13.
Figure 14B:
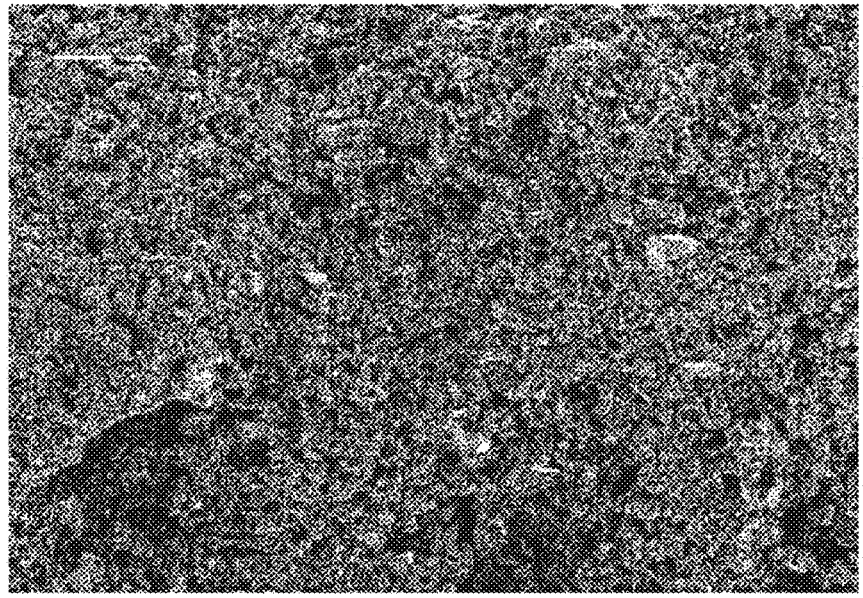
FIG. 14B is an enlarged photograph illustrating a filling result when the filling of the root canal is performed by simultaneously performing pressurization and air suction of the pressurizing part of FIG. 13.
Figure 14C:
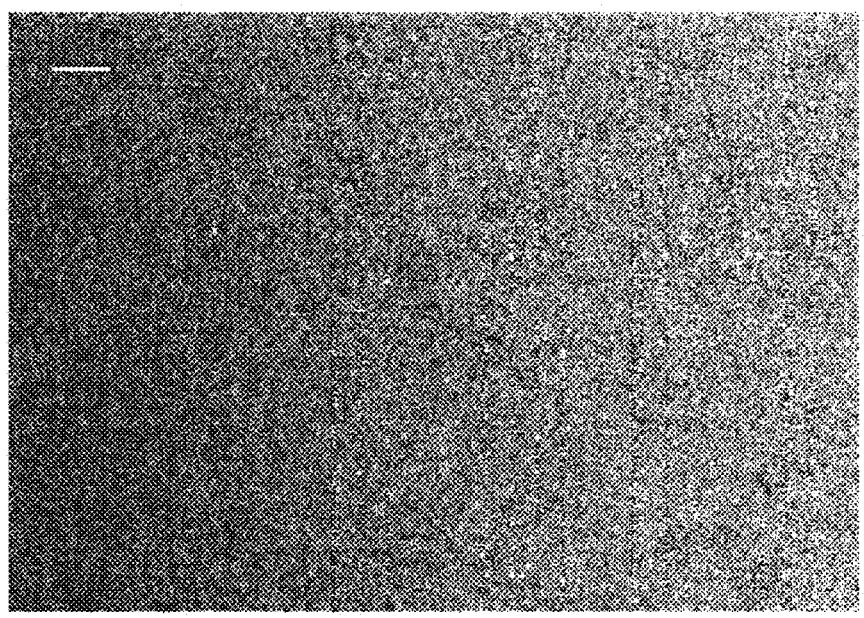
FIG. 14C is an enlarged photograph illustrating a filling result when the filling of the root canal is performed by simultaneously performing pressurization, air suction, and application of ultrasonic waves of a pressurizing part of FIG. 13 according to another embodiment.

FIG. 13 is a diagram illustrating a root canal treatment apparatus according to yet another embodiment of the present invention, and FIGS. 14A to 14C show enlarged photographs illustrating filling results when filling of the root canal is performed by a method of the root canal treatment apparatus of FIG. 13 and a conventional method.

Here, FIG. 14A is an enlarged photograph illustrating a filling result when filling of a root canal is performed with pressurization of only a pressurizing part of FIG. 13, FIG. 14B is an enlarged photograph illustrating a filling result when the filling of the root canal is performed by simultaneously performing pressurization and air suction of the pressurizing part of FIG. 13, and FIG. 14C is an enlarged photograph illustrating a filling result when the filling of the root canal is performed by simultaneously performing pressurization, air suction, and application of ultrasonic waves of a pressurizing part of FIG. 13 according to another embodiment.

Referring to FIG. 13, a root canal treatment apparatus 700 according to yet another embodiment of the present invention may include a storage container 710, an ultrasonic oscillator 720, and a nozzle 730.

The storage container 710 receives the filling material 130 from an external filling storage (not shown) to accommodate the filling material 130 in the storage container 310.

In this case, the filling material 130 used in the present invention may be formed of a flowable root canal filling material. For example, the flowable root canal filling material has a cement as a main component (about 80%) and is made of calcium silicate which has high sealingness as expanding about 2% in volume when hardened. When the flowable root canal filling material has fluidity, a type of the filling material 130 is not limited thereto.

A pressurizing part 712 pressurizes the filling material 130 in the storage container 710 to discharge the filling material 130 from the injection port 232 of the nozzle 730, which will be described below. In the present invention, as shown in the drawing, the storage container 710 and the pressurizing part 712 may be formed in a syringe shape of a the cylinder 710 and a piston 712. In this case, the piston 712 may be automatically vertically moved by a force of a motor to pressurize the filling material 130 filling in the cylinder 710.

The ultrasonic oscillator 720 applies ultrasonic waves to the filling material 130 stored in the storage container 710. Particles in the calcium silicate have high viscosity due to a strong bonding force between the inner particles. The ultrasonic waves are applied to the calcium silicate so that bonding between the inner particles of the calcium silicate may be broken. Therefore, the viscosity of the filling material 130 may be lowered by applying the ultrasonic waves to the filling material 130 by the ultrasonic oscillator 720 such that the filling material 130 may smoothly flow.

In the nozzle 730, an injection line 231, an injection port 232, and a suction port 234 may be formed in the same shape as in the nozzle 230 described above with reference to FIGS. 3 and 4. However, the present invention is not limited thereto, in the nozzle 730, an injection line 331, an injection port 332, a suction line 333, a suction port 334, an inclined line 336, and an inclined port 337 may be formed in the same shape as in the nozzle 330 described above with reference to FIGS. 6 and 7. Alternatively, the nozzle 730 may be formed in the same shape as in the nozzle 430 described above with reference to FIG. 8, the nozzle 530 described above with reference to FIGS. 9 and 10, or the nozzle 630 described above with reference to FIGS. 11 and 12.

In the present embodiment, air in the root canal 120 is suctioned through the suction port 234 and discharged to the outside. The air in the root canal 120 may act as resistance when the filling material 130 fills and may be removed through the suction port 234. As described above, since the fluidity of the filling material 130 may be improved by the ultrasonic oscillator 720, the filling material 130 may densely fill to the distal end portion of the tooth.

Hereinafter, an operation of filling the filling material 130 in the root canal 120 using the root canal treatment apparatus 700, which is described with reference to FIG. 8, will be described.

The filling material 130 may be supplied into the storage container 310 from the filling material storage (not shown) in which the filling material 130 is stored.

When the filling material 130 is supplied into the storage container 710, the filling material 130 may be pressurized by the pressurizing part 712 and discharged through the injection port 232 of the nozzle 730 due to a pressure. In this case, the ultrasonic oscillator 720 may apply the ultrasonic waves to the filling material 130 accommodated in the storage container 310 to lower the viscosity of the filling material 130. Thus, a flow characteristic of the filling material 130 may be improved.

The filling material 130 is discharged around the root canal 120 through the injection port 232 of the nozzle 730 and, simultaneously, the suction port 234 suctions the air in the root canal 120 to discharge the suctioned air to the outside.

As described above, a flow characteristic of the filling material 130 is improved by the ultrasonic oscillator 720, and the air in the root canal 120, which acts as resistance when the filling material 130 fills into the root canal 120, is removed through the suction port 234 such that the filling material 130 may densely fill up to the distal end of the tooth.

Meanwhile, in the root canal treatment apparatus 700 having the nozzle 730 provided in the same shape as the nozzle 330 described above with reference to FIGS. 6 and 7, the filling material 130 may flow together with the cleaning liquid in FIGS. 6 and 7 to densely fill the filling material 130 even in a plurality of root canals having different cross-sectional areas. Further, the root canal treatment apparatus 700 having the nozzle 730 provided in the same shape as the nozzle 330 described above with reference to FIGS. 6 and 7 may prevent the filling material 130 from leaking to the gum by passing through the root apex of the root canal.

Alternatively, the nozzle 730 may be formed in the same shape as in the nozzle 430 described above with reference to FIG. 8, the nozzle 530 described above with reference to FIGS. 9 and 10, or the nozzle 630 described above with reference to FIGS. 11 and 12 such that the filling material 130 may flow in the same form as in the cleaning liquid in the above-described nozzle 430, 530, or 630.

When the filling material 130 fills in the root canal 120 due to pressurization by only the pressurizing part 712, FIG. 14A is an enlarged photograph showing a cross section of the root canal 120 of the tooth through scanning electron microscope (SEM) imaging. When the filling material 130 fills in the root canal 120 by simultaneously performing pressurization by the pressurizing part 712 and air suction in root canal 120 by the suction port 234, FIG. 14B is an enlarged photograph showing a cross section of the root canal 120 of the tooth through the SEM imaging. When the filling material 130 fills in the root canal 120 by simultaneously performing pressurization by the pressurizing part 712, air suction in root canal 120 by the suction port 234, and ultrasonic application by the ultrasonic oscillator 720, FIG. 14C is an enlarged photograph showing a cross section of the root canal 120 of the tooth through the SEM imaging. As shown in FIG. 14C, when the pressurization by the pressurizing part 712, the air suction in the root canal 120, and the ultrasonic application are simultaneously performed, it can be seen that the filling material 130 fills very densely in the root canal 120.

Hereinafter, a root canal treatment apparatus 800 which is capable of simultaneously performing cleaning and filling of the root canal 120 with a single root canal treatment apparatus according to yet another embodiment of the present invention will be described with reference to FIG. 15.

Figure 15:
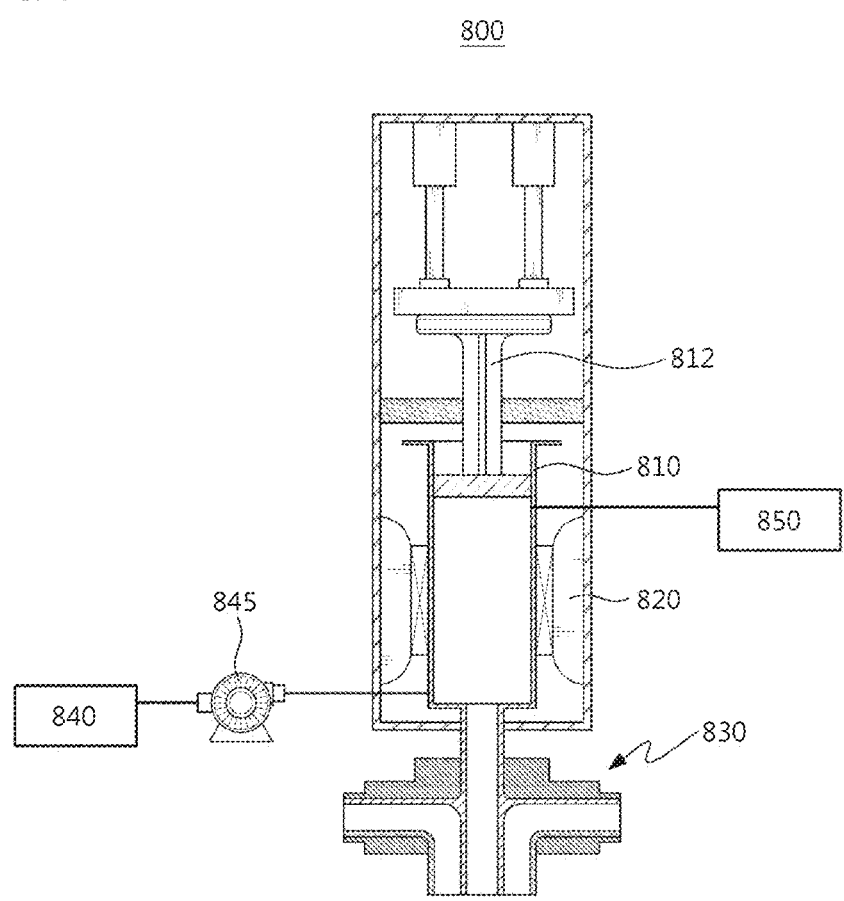
FIG. 15 is a diagram illustrating a root canal treatment apparatus according to yet another embodiment of the present invention.

FIG. 15 is a diagram illustrating a root canal treatment apparatus according to yet another embodiment of the present invention.

Referring to FIG. 15, a root canal treatment apparatus 800 according to yet another embodiment of the present invention may include a storage container 810, an ultrasonic oscillator 820, and a nozzle 830.

The storage container 810 receives a cleaning liquid stored in a cleaning liquid storage 840, which is separately provided at the outside, by the pump 845 or the like to accommodate the cleaning liquid in the storage container 410, or the storage container 410 receives the filling material 130 stored in a filling material storage 850, which is separately provided at the outside, to accommodate the filling material 130 in the storage container 410. That is, when the root canal treatment apparatus 800 of the present invention is used for cleaning the root canal 120, the cleaning liquid may be accommodated in the storage container 810, and, when the root canal treatment apparatus 400 is used for filling of the root canal 120, the filling material 130 may be accommodated in the storage container 810.

Further, as described above with reference to FIG. 13, a pressurizing part 812 may be formed in the storage container 810. Similarly, when the root canal treatment apparatus 800 is used for cleaning the root canal 120, the pressurizing part 812 may not be operated, and, when the root canal treatment apparatus 800 is used for filling of the root canal 120, the pressurizing part 812 pressurizes the filling material 130 contained in the storage container 810 to discharge the filling material 130 through the nozzle 830.

When the cleaning liquid fills in the storage container 810, the ultrasonic oscillator 820 applies ultrasonic waves to the cleaning liquid. In this case, as described above, it is preferable to generate the bubbles B. Further, as described above, when the filling material 130 fills in the storage container 810, the ultrasonic oscillator 820 may apply the ultrasonic waves to the filling material 130 to lower viscosity of the filling material 130.

In the nozzle 830, an injection line 231, an injection port 232, and a suction port 234 may be formed in the same shape as in the nozzle 230 described above with reference to FIGS. 3 and 4. However, the present invention is not limited thereto, in the nozzle 430, an injection line 331, an injection port 332, a suction line 333, a suction port 334, an inclined line 336, and an inclined port 337 may be formed in the same shape as in the nozzle 330 described above with reference to FIGS. 6 and 7. Alternatively, the nozzle 830 may be formed in the same shape as in the nozzle 430 described above with reference to FIG. 8, the nozzle 530 described above with reference to FIGS. 9 and 10, or the nozzle 630 described above with reference to FIGS. 11 and 12.

Similarly, when the root canal treatment apparatus 800 of the embodiment according to FIG. 15 is used for cleaning the root canal 120, the cleaning liquid may be suctioned through the suction port 234, and, when the root canal treatment apparatus 800 is used for filling of the root canal 120, air in the root canal 120 may be suctioned.

Hereinafter, an operation of cleaning the root canal 120 and filling the filling material 130 in the root canal 120 using the root canal treatment apparatus 800, which is described with reference to FIG. 15, will be described.

As described above, the root canal treatment apparatus 800 described with reference to FIG. 15 may be used as a device for cleaning the root canal 120 or a device for filling of the root canal 120 as necessary.

When the root canal treatment apparatus 800 is used as the device for cleaning the root canal 120, the root canal treatment apparatus 800 blocks a supply of the filling material 130 from the filling material storage 850 to the storage container 810, supplies the cleaning liquid from the cleaning liquid storage 840 to the storage container 810, and does not operate the pressurizing part 812. In this case, it is preferable to generate the bubbles B by applying the ultrasonic waves to the cleaning liquid accommodated in the storage container 810 by the ultrasonic oscillator 820. The cleaning liquid, in which the bubbles B are generated, is injected through the injection port 232 of the nozzle 830 to clean the root canal 120. Further, as described above, the cleaning liquid in the root canal 120 may be suctioned and discharged through the suction port 234 formed in the nozzle 830.

Further, when the root canal treatment apparatus 800 is used as the device for filling of the root canal 120, the root canal treatment apparatus 800 blocks the supply of the cleaning liquid from the cleaning liquid storage 840 to the storage container 810 and supplies the filling material 130 from the filling material storage 850 to the storage container 810. When an interior of the storage container 810 is filled with the filling material 130, the pressurizing part 812 is operated to discharge the filling material 130 around the root canal 120 through the injection port 232 of the nozzle 830. In this case, the ultrasonic oscillator 820 may apply the ultrasonic waves to the filling material 130 in the storage container 810 to lower viscosity of the filling material 130 having high viscosity such that a flow characteristic of the filling material 130 may be improved. As described above, while the filling material 130 fills in the root canal 120, the air in the root canal 120 is suctioned through the suction port 234 such that the filling material 130 may fill more densely in the root canal 120.

Meanwhile, in the root canal treatment apparatus 800 having the nozzle 830 provided in the same shape as the nozzle 330 described above with reference to FIGS. 6 and 7, the cleaning liquid may clean a plurality of root canals having different cross-sectional areas. Further, in the root canal treatment apparatus 800, the filling material 130 may flow together with the cleaning liquid in FIGS. 6 and 7 to densely fill the filling material 130 even in a plurality of root canals having different cross-sectional areas. Further, the root canal treatment apparatus 800 having the nozzle 830 provided in the same shape as the nozzle 330 described above with reference to FIGS. 6 and 7 may prevent the cleaning liquid or the filling material 130 from leaking to the gum by passing through the root apex of the root canal.

Alternatively, the nozzle 830 may be formed in the same shape as in the nozzle 430 described above with reference to FIG. 8, the nozzle 530 described above with reference to FIGS. 9 and 10, or the nozzle 630 described above with reference to FIGS. 11 and 12 such that the cleaning liquid and the filling material 130 may flow in the same form as in the cleaning liquid in the above-described nozzle 430, 530, or 630.

As described above, although the exemplary embodiments have been described with reference to the accompanying drawings, various alternations and modifications can be derived by those skilled in the art from the above description of the present invention. For example, it should be understood that an appropriate result may be achieved even when the techniques described herein may be performed in a different order than the described methods, and/or that components of the described structures, devices, and the like are coupled or combined in a form different from the described methods, or substituted or replaced with other components or equivalents.

What is claimed is:
1. A root canal treatment apparatus, comprising:
a storage container configured to store a cleaning liquid which is supplied from the outside of the root canal treatment apparatus;
an ultrasonic oscillator configured to apply ultrasonic waves to the cleaning liquid stored in the storage container and adjust a frequency of the ultrasonic oscillator to generate bubbles in the cleaning liquid stored in the storage container; and a nozzle including an injection line, wherein a first end of the injection line is connected to the storage container and a second end of the injection line is configured to output the cleaning liquid, including the generated bubbles, the outside of the root canal treatment apparatus, wherein a cross sectional area of the injection line is smaller than a cross sectional area of the storage container such that sizes of the bubbles in the cleaning liquid at the second end of the injection line are smaller than sizes of the bubbles in the cleaning liquid stored in the storage container, wherein the root canal treatment apparatus is capable of cleaning the root canal, wherein the nozzle further includes an inclined line in which an inclined port for injecting the cleaning liquid from the injection port, at an inclined angle from 0° to 90° is formed and which is formed to protrude from one end of the injection line, and wherein the inclined port is provided as a plurality of holes formed at an end of the inclined line.

2. The root canal treatment apparatus of claim 1, wherein:
the second end of the injection line includes an injection port;
the nozzle includes a suction port;
the injection port of the nozzle is formed as a hole passing straight through the nozzle; and
the suction port of the nozzle is formed in an annular shape to surround the injection port.

3. A root canal treatment apparatus, comprising:
a storage container configured to store a filling material for filling of a root canal;
an ultrasonic oscillator configured to apply ultrasonic waves to the filling material stored in the storage container; and a nozzle including an injection line, wherein a first end of the injection line is connected to the storage container and a second end of the injection line is configured to discharge the filling material toward a root canal;

a suction line with a suction port for suctioning air in the root canal; and a pressurizing part configured to pressurize the filling material in the storage container and to discharge the filling material through the nozzle, wherein the root canal treatment apparatus is configured to simultaneously operate the ultrasonic oscillator to apply ultrasonic waves to the filling material to lower the viscosity of the filing material, operate the pressurizing part to pressurize the filling material with lowered viscosity to be discharged through the nozzle, and operate the suction line to suction air in the root canal, wherein the nozzle further includes an inclined line with an inclined port for injecting the filling material, which is injected from the injection port at an inclined angle from 0° to 90°, and wherein the injected port protrudes from one end of the injection, wherein the inclined port is provided as one or more inclined ports which are radially formed from a center of one end of the injection port, and wherein the inclined port is provided as a plurality of holes formed at an end of the inclined line.

4. The root canal treatment apparatus of claim 3, wherein the filling material is formed of flowable root canal filling materials.

5. The root canal treatment apparatus of claim 3, wherein:
the second end of the injection line includes an injection port;
the nozzle includes a suction port;
the injection port of the nozzle is formed as a hole passing straight through the nozzle; and
the suction port of the nozzle is formed in an annular shape to surround the injection port.

* * * * *